United States Patent [19]
Schraga

[11] Patent Number: 5,464,418
[45] Date of Patent: Nov. 7, 1995

[54] REUSABLE LANCET DEVICE

[76] Inventor: Steven Schraga, 1841 NE. 146 St., North Miami, Fla. 33181

[21] Appl. No.: 163,514

[22] Filed: Dec. 9, 1993

[51] Int. Cl.⁶ .................................................. A61B 17/34
[52] U.S. Cl. ............................................. 606/182; 606/171
[58] Field of Search ................................. 606/181, 182, 606/183, 185, 167; 604/136, 157, 218

[56] References Cited

U.S. PATENT DOCUMENTS

| | | | |
|---|---|---|---|
| 4,139,011 | 2/1979 | Benoit et al. | 606/182 |
| 4,379,456 | 4/1983 | Cornell et al. | 606/182 |
| 4,449,529 | 5/1984 | Burns et al. | 606/182 |
| 4,517,978 | 5/1985 | Levin et al. | 606/182 |
| 4,895,147 | 1/1990 | Bodicky et al. | 606/182 |
| 5,147,375 | 9/1992 | Sullivan et al. | 606/182 |
| 5,269,799 | 12/1993 | Daniel | 606/182 |

FOREIGN PATENT DOCUMENTS 1126718  11/1956  France .................................. 604/218

*Primary Examiner*—Stephen C. Pellegrino
*Assistant Examiner*—Nancy Mulcare
*Attorney, Agent, or Firm*—Malloy & Malloy

[57] ABSTRACT

An improved, reusable lancet device, to be utilized with a disposable lancet, the device having an elongate triangular housing and a triangular cap segment to be matingly fitted with one another, the housing and cap segment being adapted to contain an elongate needle holding member slidably disposed within a channel of the housing, the needle holder member having a distal segment, a central segment, and a proximal segment, the proximal segment being adapted to hold the disposable lancet such that a point thereof is positioned in a ready to use position extending away from the housing. The needle holding member is movable between a cocked, retracted position and an extended position, and is disposed within the housing such that it will not be able slide out of the housing, yet during use, can be released from its cocked, retracted position so as to immediately move to the extended position wherein the point of the disposable lancet protrudes through a piercing opening disposed in the cap segment so as to be in a piercing position.

6 Claims, 2 Drawing Sheets

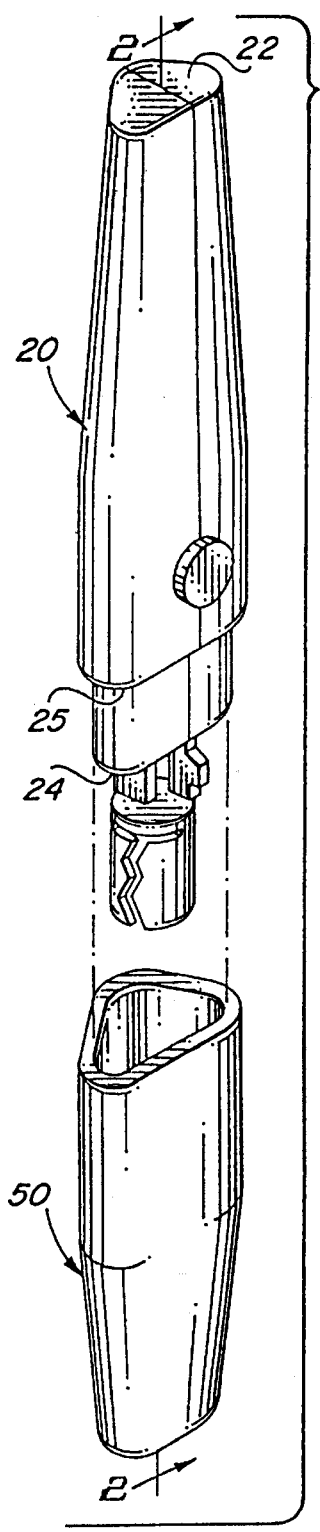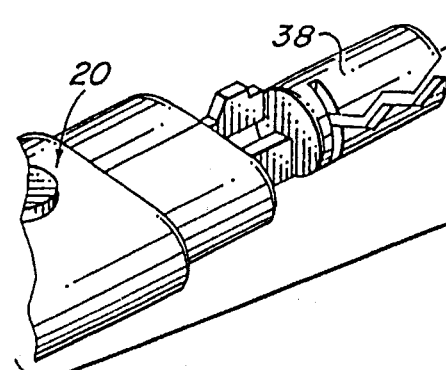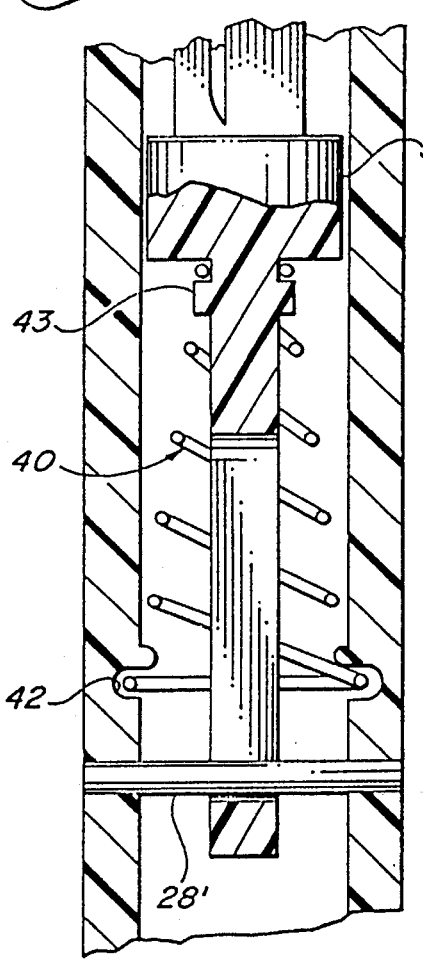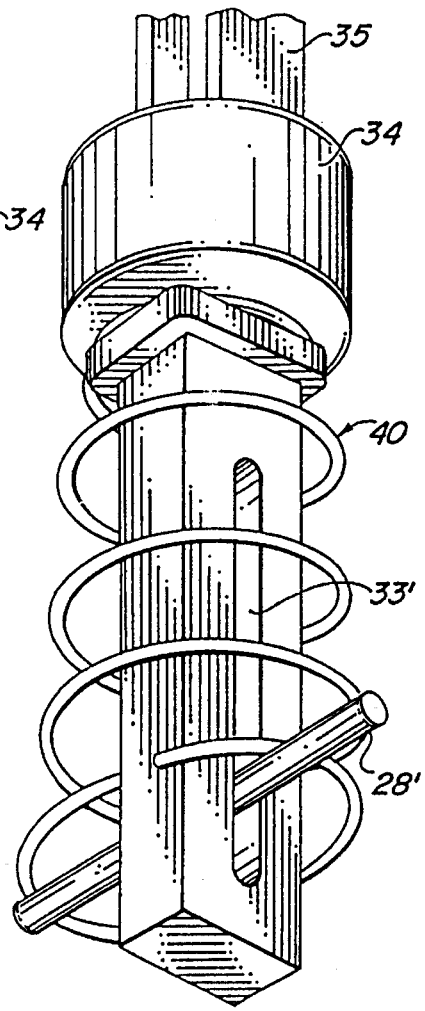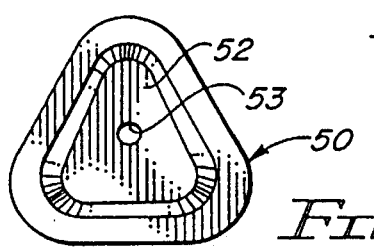

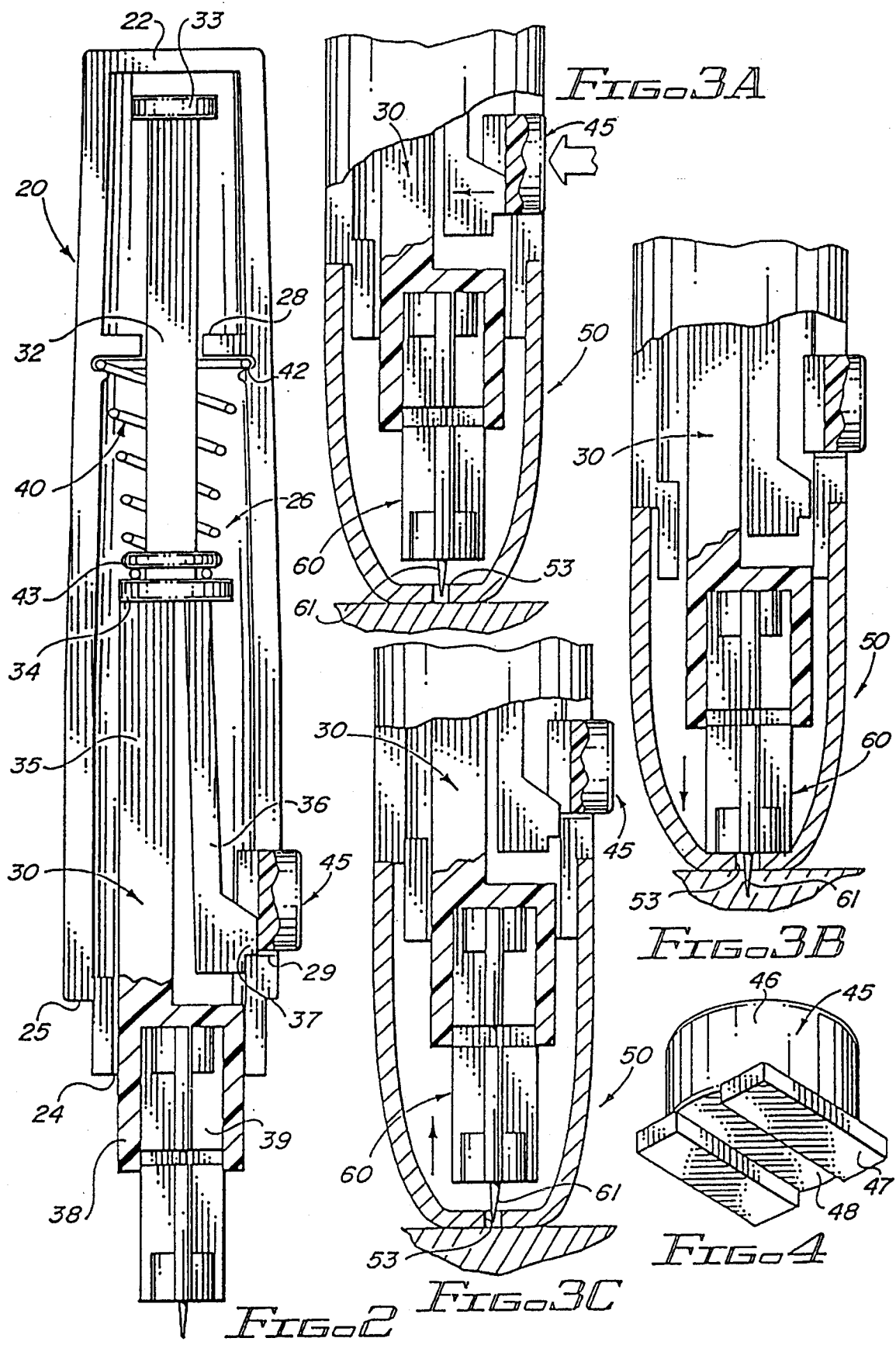

REUSABLE LANCET DEVICE

BACKGROUND OF THE INVENTION

1. Field of the Invention

The present invention relates to a reusable lancet device adapted to be substantially inexpensive to manufacture and easy and safe to use by physically impaired individuals who must take their own blood samples.

2. Description of the Related Art

The field of art relating to disposable and reusable lancet devices is substantially crowded. Further, due to the nature of the devices, seemingly small improvements relating to safety in use and minimizing consumer cost provide significant improvements over prior devices. This is evident by the numerous patents issued for varying types of lancet devices, such as those disclosed in the patents to Sullivan, et al., U.S. Pat. No. 5,147,375, Dombrowski, U.S. Pat. No. 4,653,513, Burns, U.S. Pat. No. 4,527,561, and Levin, et al., U.S. Pat. No. 4,517,978. Specifically, the patent to Sullivan, et al. provides for improved spring retraction; The patent to Burns provides for stronger and quicker needle impact; The patent to Dombrowski provides for the ability to prick other parts of a user's body rather than a finger; and the reference to Levin, et al. provides for a removable cap to facilitate interchanging of a needle, an annular flange to facilitate the device being pressed against a finger, and a single trigger which needs to be pressed. There are, however, additional, important factors relating to the safe and effective use of lancet assemblies which have not been addressed by the prior art. Specifically, there is a need for a lancet device which will not unnecessarily roll around in a user's hand or on a table due to its configuration, yet will also be structured such that the cap will always be properly positioned atop the housing, even by impaired individuals who will not be able to pay close attention to detail. Further, known reusable lancet devices employ a relatively large number of individual pieces, thereby making them more expensive to manufacture and minimizing their availability to independent patient users who must test there own blood. Also, known reusable lancet devices employ plunger-type apparatuses wherein after a cap is replaced to contain the lancet, a plunger is pulled to place the lancet tip in a cocked, ready-to-use position. Such plunger-type structuring is unnecessary and may cause difficulties in use, primarily because after the plunger is pulled, it may slide freely within the housing until the lancet is triggered and the plunger is pulled forward during which it can potentially catch on a user's hand or clothing so as to pitch them or resist the firing of the lancet such that it will not have the velocity necessary to properly pierce the skin and retract into the housing.

Accordingly, it would be highly beneficial in the art to provide a reusable lancet device which due to its shape and configuration will not unnecessarily roll around in a user's hand or on a flat surface, yet will provide for a cap which will always be properly positioned when it is placed on the housing. Further, it would be highly beneficial to provide a reusable lancet device which does not include a movable plunger which could restrict the movement of a lancet contained therein, but rather utilizes the positioning of the single use, disposable lancet tip within the lancet device to retract the lancet tip into a cocked, ready-to-use position.

The device of the present invention is designed specifically to meet the needs still evidenced in the use of reusable lancet devices. These devices, which are often utilized by infirmed individuals to do their own routine blood test, require precise adaptation to make them effective yet completely safe for the user. Also, the device of the present invention is adapted with a small number of individual pieces, thereby making the reusable lancet device easier and substantially more cost effective to manufacture and provide for use by patients, without compromising any of the safety needs and in fact increasing the safety of use.

SUMMARY OF THE INVENTION

The present invention is directed towards an improved reusable lancet device to be utilized with a disposable lancet. The reusable lancet device includes an elongate triangular housing adapted to fit within the user's hand. This housing includes a closed first end, an open second end, and an elongate channel therein which extends from the first end to the second end. Disposed within this elongate channel is an elongate needle holding member. This needle holding member is movable between a cocked, retracted position and an extended position. The needle holding member, which includes a distal segment, a central segment, and a proximal segment, is disposed within the housing such that the proximal segment protrudes through the open second end of the housing. The proximal segment is structured to hold a disposable lancet therein, the disposable lancet being positioned within the proximal segment such that a point thereof extends away from the needle holding member and is thus in a ready-to-use position. Further disposed within the housing are biasing means. The biasing means are adapted to urge the needle holding member into the extended position when not held in a retracted position. Stopper means are also included to limit an amount which the needle holding member is allowed to protrude through the open second end of the housing, and to prevent axial movement of the needle holding member within the housing. Utilizing the stopper means, the needle holding member will always be retained within the channel despite its movement from the cocked, retracted position to the extended position. In order to hold the needle holding member in the cocked, retracted position, and accordingly hold the biasing means in a retracted position, trigger means are employed. The trigger means hold the needle holding member in the cocked, retracted position until release by a user which will result in an immediate movement of the needle holding member to the extended position as a result of the functioning of the biasing means. Finally, the lancet device includes a triangular cap segment with an open first side and a closed second side containing a piercing opening therein. The open first side is adapted to be matingly fitted over the open second end of the housing, thereby containing the needle holder member and disposable lancet therein. When in a cocked, retracted position, or after use, the needle holding member is disposed such that the point of the disposable lancet is concealed within the cap segment. During use, upon release by the trigger means, the needle holding member is immediately moved to the extended position wherein the point of the disposable lancet will momentarily extend through the piercing opening into a piercing position which punctures a hole in a user's skin and then retracts back beneath the cap segment.

It is an object of the present invention to provide a reusable lancet device which is substantially cost effective to manufacture due to a small number of individual pieces to be put together, yet will still be substantially safe during use.

Still another object of the present invention is to provide an improved reusable lancet device which provides for facilitated and effective cap positioning by impaired individuals.

Yet another object of the present invention is to provide an improved reusable lancet device which is comfortably positionable within a user's hand and will not roll around within a user's hand or a flat surface.

A further object of the present invention is to provide an improved reusable lancet device which does not necessitate that an exteriorly exposed plunge assembly be utilized in order to position the lancet in a retracted, ready-to-use position.

BRIEF DESCRIPTION OF THE DRAWINGS

For a fuller understanding of the nature of the present invention, reference should be had to the following detailed description taken in connection with the accompanying drawings in which:

FIG. 1 is a partially exploded perspective view of the reusable lancet device of the present invention.

FIG. 2 is a cross-sectional view along line 2—2 of FIG. 1.

FIGS. 3A, 3B, and 3C are isolated, cross-sectional views of the improved reusable lancet device illustrating the functioning of the lancet.

FIG. 4 is an isolated view of the trigger button of the reusable lancet device of the present invention.

FIG. 5 is a bottom plan view of the triangular cap segment of the reusable lancet device of the present invention.

FIG. 6 is an isolated perspective view of the reusable lancet device illustrating the positioning of a disposable lancet therein.

FIG. 7 is an isolated cross-sectional view illustrating the positioning of the biasing means of the reusable lancet device of the present invention.

FIG. 8 is an isolated perspective view of the second embodiment of the stopper means of the reusable lancet device.

Like reference numerals refer to like parts throughout the several views of the drawings.

DETAILED DESCRIPTION OF THE PREFERRED EMBODIMENT

Shown throughout FIGS. 1–8, the present invention is directed towards an improved reusable lancet device, generally indicated as 10. The reusable lancet device 10 is preferably formed of a lightweight, rigid, and substantially inexpensive plastic material and is adapted for use with a standard type disposable lancet 60. The reusable lancet device 10 includes primarily an elongate, substantially triangular shaped housing 20. The housing 20 includes the substantially triangular shape, with slightly rounded corners, such that it will be easy to manipulate and will not unnecessarily roll around within a user's hand, especially if the user is sick, old, or otherwise impaired.

The elongate triangular housing 20, as illustrated in FIG. 2, includes a closed first end 22, an open second end 24, and an elongate channel 26. Further, the housing 20 is preferably molded of two halves to be joined together, so as to facilitate manufacture. The elongate channel 26 extends from the closed first end 22 to the open second end 24. Slidably positioned within the channel 26 is an elongate needle holding member 30. This needle holding member 30, which is movable between a cocked, retracted position, illustrated in FIG. 2, and an extended position, illustrated in FIG. 3B, includes three segments. Specifically, the needle holder member 30 is formed of a distal segment 32, a central segment 35, and a proximal segment 38. The proximal segment 38, which protrudes from the open second end 24 of the housing 20 is adapted to hold the disposable lancet 60 therein. Specifically, the disposable lancet 60 is of the type which includes a main body 65 and a point 61, which until use is contained within a protective cap 62. When used, the body 65 is inserted into an interior 39 of the proximal segment 38, as illustrated in FIG. 8, then the protective cap 62 is pulled from the point 61. The disposable lancet 60 is held in the proximal segment 38 such that the point 61 points away from the housing and such that sliding movement of the needle holding member 30 will result in corresponding movement of the disposable lancet 60. The overall sliding and axial movement of the needle holding member 30 is regulated by stopper means. In the preferred embodiment, detailed in FIG. 2, the stopper means include a guide collar 28 disposed within the housing 20. The guide collar 28 is adapted to receive the distal segment 32 of the needle holding member 30 slidably therethrough. The needle holding member 30 is preferably flat such that it will slide through the guide collar 28, but will not rotate axially therein, thereby assuring that the needle holding member 30 will remain properly oriented when moved into its cocked, retracted position. Further, the guide collar 28 is sized to retain a flanged end 33 of the distal segment 32 of the needle holding member 30 between the closed first end 22 of the housing 20 and the guide collar 28. In this manner, inward movement of the needle holding member within the housing 20 is limited by the flanged end 33 contacting the closed first end 22 of the housing 20, and outward movement of the needle holding member 20 is limited by the flanged end 33 of the distal segment 32 contacting the guide collar 28. In this manner, the needle holding member 30 will be retained within the channel 26.

Turning to FIG. 8, an alternative embodiment of the stopper means includes an elongate slot 33' disposed in the distal segment 32 of the needle holding member 35. The slot is positioned such that a peg 28' which extends from an interior of the housing 20 passes therethrough. The peg 28' remains within the elongate slot 33' at all times thereby limiting movement of the needle holding member 30 to a length of the slot 33' and assuring that the needle holding member 30 is retained within the channel 26 of the housing 20. Also, positioning of the peg 28' within the slot 33' will not allow axial rotation of the needle holding member 30.

So as to contain and shield the exposed point 61 of the disposable lancet 60, a triangular cap segment 50 is included. The triangular cap segment 50 includes an open first side 51 and a closed second side 52. The cap segment is adapted to have substantially the same configuration as the housing 20 and is sized such that the open first side 51 is matingly fitted over the open second end 24 of the housing 20. Further, the open second end 24 of the housing 20 extends from a lip 25 formed in the housing 20, the lip 25 being disposed such that the open first side 51 of the cap segment 50 slides onto the housing 20 over the open second end 24 of the housing 20 and will abut the lip 25 providing a smooth contoured finish. The cap segment 50 will be removably fitted on the housing 20 preferably through corresponding proportioning of an interior dimension of the open first side 51 of the cap segment 50 relative to the open second end 24 of the housing 20, but alternatively engagement ridges or like removable fastening means may be included to secure the cap segment 50 on the housing 20. Disposed in the closed second side 52 of the cap segment 50 is a piercing opening 53. The piercing opening 53 is positioned such that when the needle holding member 30, containing a disposable lancet 60 therein, is moved to its fully extended position, the point 61 of the disposable lancet 60 will protrude through the piercing opening 53 to puncture a desired surface. See FIG. 3B.

So as to move the needle holding member 30 from its cocked, retracted position to its fully extended position, biasing means are included. The biasing means are preferably in the form of a spring 40 disposed about the distal segment 32 of the needle holding member 30. The spring 40 is positioned such that it will abut a flanged lip 34 formed in the needle holding member 30 and will abut the housing 20. Preferable a side of the spring 40 which abuts the housing 20 will have a larger relaxed diameter than an opposite side of the spring 40. In the first embodiment, illustrated in FIGS. 2 and 7, one end of the spring 40 is positioned to contact the guide collar 28 of the housing 20 and is preferably embedded in an annular ridge 42 formed in the housing 20. The opposite side of the spring 40, which abuts the needle holding member 30 is preferably contained within an annular ridge 43 formed at the flanged lip 34. In the alternative embodiment of the stopper means illustrated in FIGS. 7 and 8, the spring 40 abuts the housing 20 at the peg 28' which is positioned through the slot 33' in the distal segment 32. With the spring 40 positioned appropriately, when extended, it will urge the needle holding member 30 towards the open second end 24 of the housing 20. When the needle holding member 30 is in its retracted, cocked position, as detailed in FIG. 2, the spring 40 is compressed. Once the needle holding member 30 is allowed to move to its extended position, the spring 40 will quickly and immediately move the needle holding member 30 to the fully extended position with the point 61 of the disposable lancet tip 60 protruding through the piercing opening 53 in the cap segment 52. After this initial release and movement to its fully extended position, the spring 40 relaxes such that the needle holding member 30 will move slightly back towards the closed first end 22 of the housing 20, as illustrated in FIG. 3C, into a relaxed position wherein the point 61 of the disposable lancet 60 is contained within the cap segment 50 and will not accidentally contact a user unnecessarily.

In order to hold the needle holding member 30 in its cocked, retracted position, and subsequently allow release by a user in order to initiate movement of the needle holding member 30 to its extended position, trigger means are included. The trigger means preferably include an aperture 29 formed in the housing 20 near the open second end 24 thereof. Also included as part of the trigger means is an outwardly biased engagement segment 36 which extends from the central segment 35 of the needle holding member 30. The engagement segment 36 includes a distal lip segment 37 which contacts an interior of the housing 20 as the needle holding member 30 slides within the channel 26. Contact is made due to the outwardly biasing nature of the engagement segment 36, and when the needle holding member 30 is pushed into the housing 20 so as to be in its retracted, cocked position, the distal lip segment 37 extends upwardly into the aperture 29 formed in the housing 20 so as to contact the housing 20 inside the aperture 29 and maintain the needle holding member 30 in its retracted, cocked position and the spring 40 in its compressed position. In order to release the needle holding member 30 from its retracted, cocked position, the engagement segment 36 must be pushed such that the distal lip segment 37 exits the aperture 29 and the needle holding member 30 can move freely to its fully extended position due to the biasing force of the spring 40. In order to push the engagement segment 36, a trigger button 45 is disposed within the aperture 29. The trigger button 45, as detailed in FIG. 4, includes an upper section 46 which protrudes through the aperture 29 to an exterior of the housing 20 and a flanged base portion 47 which is disposed within the housing 20 so as to assure that the trigger button 45 does not get pushed out of the housing 20 through the aperture 29. Disposed within the base 47 is a channel 48 positioned such that the distal lip segment 37 of the engagement segment 36 will slide therethrough and be able to engage the housing 20 within the aperture 29.

The reusable lancet device 10 of the present invention, as recited, includes only five distinct pieces and the spring 40 which must be assembled during manufacturing. These five distinct pieces include both halves of the housing 20, the needle holding member 30, the trigger button 45, and the cap segment 50. The use of such a small number of pieces enables quick and substantially inexpensive manufacturing of the reusable lancet device 10 of the present invention, thereby making a more cost effective product which can be available to the public without compromising safety. During use, the needle holding member 30 is moved to its retracted, cocked position by removing the cap segment 50, placing the disposable lancet 60 within the needle holding member 30, and pushing the disposable lancet 60 and accordingly the needle holding member 30 into the housing 20 until the trigger means are engaged. Once properly positioned, the protective cap 62 can be removed from the disposable lancet 60 so as to expose a point 61, and the cap segment 50 is replaced thereover. Due to the triangular shape, the cap segment 50 will securely and properly fit over the housing 20 no matter which orientation a user utilizes to push the cap segment 50 onto the housing 20. After a single use of the disposable lancet 60, the cap 50 is removed, the disposable lancet 60 is removed and discarded appropriately, and the reusable lancet device 10 of the present invention is ready for an additional use.

Now that the invention has been described,
What is claimed is:
1. To be used with a disposable lancet, an improved, reusable lancet device comprising:
an elongate housing of triangular cross-section,
said housing including a closed first end, an open second end, and an elongate channel therein extending from said first end to said second end,
an elongate needle holding member disposed within said channel and being movable therein between a cocked, retracted position and an extended position,
said needle holder member including a distal segment, a central segment, and a proximal segment,
said proximal segment being structured and disposed to protrude from said open second end of said housing and to hold the disposable lancet therein such that a point of the disposable lancet extends away from said needle holding member,
biasing means structured and disposed to urge said needle holding member into said extended position, said biasing means including a spring disposed about said distal segment of said needle holding member, said spring abutting a flanged lip formed in said needle holding member between said distal segment and said central segment such that extension of said spring results in corresponding movement of said needle holding member,
stopper means structured and disposed to limit an amount which said needle holding member moves axially and an amount which said needle holding member will protrude through said open second end of said housing, thereby retaining said needle holding member within said channel, said stopper means including an elongate slot disposed in said distal segment of said needle holding member, and a peg extending from an interior of said housing through said slot so as to limit movement of said needle holding member to a length of said slot, trigger means structured and disposed to maintain said needle holding member in said cocked, retracted position until released by a user, releasing by the user resulting in immediate movement of said needle holding member to said extended position, and a cap segment of triangular cross-section including an open first side structured and disposed to be matingly fitted over said open second end of said housing, and a piercing opening disposed in a second side thereof, said piercing opening being structured and disposed to enable the point of the lancet to extend therethrough into a piercing position upon release of said needle holding member from said cocked, retracted position.

2. A reusable lancet device as recited in claim 1 wherein said trigger means includes:

a trigger button, an aperture disposed in said housing, said aperture being structured and disposed to receive said trigger button therein, and an outwardly biased engagement segment extending from said central segment of said needle holder member and structured and disposed to extend into said aperture in said housing so as to retain said needle holding member in said cocked, retracted position and said spring in a compressed position, and be pushed out of said aperture by said trigger button so as to release said needle holding member and enable said needle holding member to move to said extended position.

3. A reusable lancet device as recited in claim 2 formed of only six distinct pieces so as to facilitate manufacturing and minimize costs.

4. To be used with a disposable lancet, an improved, reusable lancet device comprising:

an elongate housing, said housing including a closed first end, an open second end, and an elongate channel therein extending from said first end to said second end, an elongate needle holding member disposed within said channel and being movable therein between a cocked, retracted position and an extended position, said needle holder member including a distal segment, a central segment, and a proximal segment, said proximal segment being structured and disposed to protrude from said open second end of said housing and to hold the disposable lancet therein such that a point of the disposable lancet extends away from said needle holding member, biasing means structured and disposed to urge said needle holding member into said extended position, said biasing means including a spring disposed about said distal segment of said needle holding member, said spring abutting a flanged lip formed in said needle holding member between said distal segment and said central segment such that extension of said spring results in corresponding movement of said needle holding member, stopper means structured and disposed to limit an amount which said needle holding member moves axially and an amount which said needle holding member will protrude through said open second end of said housing, thereby retaining said needle holding member within said channel, said stopper means including an elongate slot disposed in said distal segment of said needle holding member, and a peg extending from an interior of said housing through said slot so as to limit movement of said needle holding member to a length of said slot, trigger means structured and disposed to maintain said needle holding member in said cocked, retracted position until released by a user, releasing by the user resulting in immediate movement of said needle holding member to said extended position, and a cap segment including an open first side structured and disposed to be matingly fitted over said open second end of said housing, and a piercing opening disposed in a second side thereof, said piercing opening being structured and disposed to enable the point of the lancet to extend therethrough into a piercing position upon release of said needle holding member from said cocked, retracted position.

5. To be used with a disposable lancet, an improved reusable lancet device comprising:

an elongate housing, said housing including a closed first end, an open second end, and an elongate channel therein extending from said first end to said second end, an elongate needle holding member disposed within said channel and being movable therein between a cocked, retracted position and an extended position, said needle holder member including a distal segment, a central segment, and a proximal segment, said proximal segment being structured and disposed to protrude from said open second end of said housing and to hold the disposable lancet therein such that a point of the disposable lancet extends away from said needle holding member, biasing means structured and disposed to urge said needle holding member into said extended position, said biasing means including a spring disposed about said distal segment of said needle holding member, said spring abutting a flanged lip formed in said needle holding member between said distal segment and said central segment such that extension of said spring results in corresponding movement of said needle holding member, stopper means structured and disposed to limit an amount which said needle holding member moves axially and an amount which said needle holding member will protrude through said open second end of said housing, thereby retaining said needle holding member within said channel, said stopper means including a guide collar disposed within said housing, said guide collar being structured and disposed to facilitate sliding movement of said distal segment of said needle holding member therethrough and to retain a flanged end of said distal segment of said needle holding member between said guide collar and said closed first end of said housing such that said needle holding member cannot slide out of said housing through said open second end, said spring being disposed between said flanged lip in said needle holding member and said guide collar, said spring being fixedly secured at one end thereof to said housing at said guide collar, trigger means structured and disposed to maintain said needle holding member in said cocked, retracted position until released by a user, releasing by the user resulting in immediate movement of said needle holding member to said extended position, and a cap segment including an open first side structured and disposed to be matingly fitted over said open second end of said housing, and a piercing opening disposed in a second side thereof, said piercing opening being structured and disposed to enable the point of the lancet to extend therethrough into a piercing position upon release of said needle holding member from said cocked, retracted position.

6. A reusable lancet device as recited in claim 5 wherein said housing and said cap segment are each of triangular cross-section.

* * * * *